(12) United States Patent
Trieu

(10) Patent No.: US 9,039,765 B2
(45) Date of Patent: May 26, 2015

(54) IMPLANT SYSTEM AND METHOD FOR STABILIZATION OF A SACRO-ILIAC JOINT

(75) Inventor: Hai H. Trieu, Cordova, TN (US)

(73) Assignee: Warsaw Orhtopedic, Inc., Warsaw, IN (US)

( * ) Notice: Subject to any disclaimer, the term of this patent is extended or adjusted under 35 U.S.C. 154(b) by 1128 days.

(21) Appl. No.: 13/011,024

(22) Filed: Jan. 21, 2011

(65) Prior Publication Data

US 2012/0191191 A1 Jul. 26, 2012

(51) Int. Cl.
| | | |
|---|---|---|
| A61F 2/44 | (2006.01) | |
| A61B 17/68 | (2006.01) | |
| A61B 17/86 | (2006.01) | |
| A61B 17/70 | (2006.01) | |
| A61F 2/30 | (2006.01) | |

(52) U.S. Cl.
CPC ..... *A61B 17/683* (2013.01); *A61F 2002/30995* (2013.01); *A61B 17/863* (2013.01); *A61B 17/8685* (2013.01); *A61B 17/8695* (2013.01); *A61B 17/7055* (2013.01)

(58) Field of Classification Search
CPC .................. A61F 2/4611; A61F 2/442; A61F 2002/30995
USPC ..................................................... 623/17.11
See application file for complete search history.

(56) References Cited

U.S. PATENT DOCUMENTS

| | | |
|---|---|---|
| 2,077,804 A | 4/1937 | Morrison |
| 2,489,870 A | 11/1949 | Dzus |
| 4,463,753 A | 8/1984 | Gustilo |
| 4,640,271 A | 2/1987 | Lower |
| 5,217,462 A | 6/1993 | Asnis et al. |
| 5,242,444 A | 9/1993 | MacMillan |
| 5,334,205 A | 8/1994 | Cain |
| 5,498,265 A | 3/1996 | Asnis et al. |
| 5,743,914 A | 4/1998 | Skiba |
| 5,989,255 A | 11/1999 | Pepper et al. |
| 6,053,916 A | 4/2000 | Moore |
| 6,620,196 B1 | 9/2003 | Trieu |
| 6,733,531 B1 | 5/2004 | Trieu |
| 6,887,243 B2 | 5/2005 | Culbert |
| 6,893,466 B2 | 5/2005 | Trieu |
| 6,899,719 B2 | 5/2005 | Reily et al. |
| 6,974,479 B2 | 12/2005 | Trieu |
| 7,445,634 B2 | 11/2008 | Trieu |
| 7,556,629 B2 * | 7/2009 | von Hoffmann et al. ....... 606/67 |
| 7,648,509 B2 | 1/2010 | Stark |
| 7,824,429 B2 | 11/2010 | Culbert et al. |
| 2002/0087161 A1 | 7/2002 | Randall et al. |
| 2003/0097132 A1 | 5/2003 | Padget et al. |
| 2005/0137595 A1 | 6/2005 | Hoffmann et al. |

(Continued)

*Primary Examiner* — Nicholas Woodall
*Assistant Examiner* — Christine Nelson

(57) ABSTRACT

A sacro-iliac implant includes a body extending from a first portion having an outer surface configured for fixation with a sacrum to a second portion having an outer surface being spaced apart and non-continuous with the outer surface of the first portion. A sleeve is disposed about the body and configured for implantation within at least an ilium. The sleeve extends from a first portion to a second portion having an inner surface and a flange disposed to engage an outer non-articular surface of the ilium. The inner surface of the second portion of the sleeve is engageable with the outer surface of the second portion of the body to cause axial translation of the body relative to the sleeve such that naturally separated articular surfaces of the sacrum and ilium are drawn into fixation to immobilize the SI joint. Methods of use are disclosed.

16 Claims, 6 Drawing Sheets

(56) References Cited

U.S. PATENT DOCUMENTS

| | | |
|---|---|---|
| 2006/0015105 A1 | 1/2006 | Warren et al. |
| 2006/0047341 A1 | 3/2006 | Trieu |
| 2006/0085002 A1 | 4/2006 | Trieu et al. |
| 2006/0089647 A1 | 4/2006 | Culbert et al. |
| 2006/0095134 A1 | 5/2006 | Trieu et al. |
| 2006/0106382 A1 | 5/2006 | Gournay et al. |
| 2006/0161154 A1 | 7/2006 | McAfee |
| 2006/0229612 A1* | 10/2006 | Rothman et al. ............. 606/61 |
| 2007/0021801 A1 | 1/2007 | Heruth et al. |
| 2007/0142842 A1 | 6/2007 | Krueger et al. |
| 2007/0213660 A1 | 9/2007 | Richards et al. |
| 2007/0265621 A1 | 11/2007 | Matthis et al. |
| 2008/0009861 A1 | 1/2008 | Stark |
| 2008/0021463 A1 | 1/2008 | Georgy |
| 2008/0039843 A1 | 2/2008 | Abdou |
| 2008/0154306 A1 | 6/2008 | Heinz |
| 2009/0024174 A1 | 1/2009 | Stark |
| 2009/0069813 A1 | 3/2009 | von Hoffmann et al. |
| 2009/0076517 A1 | 3/2009 | Reiley et al. |
| 2009/0093817 A1 | 4/2009 | Zucherman et al. |
| 2009/0099610 A1 | 4/2009 | Johnson et al. |
| 2009/0131950 A1* | 5/2009 | Liu et al. ................... 606/94 |
| 2009/0149860 A1 | 6/2009 | Scribner et al. |
| 2009/0181892 A1 | 7/2009 | Thorne et al. |
| 2009/0216238 A1 | 8/2009 | Stark |
| 2009/0259261 A1 | 10/2009 | Reiley |
| 2009/0263321 A1 | 10/2009 | McDonald et al. |
| 2009/0263459 A1 | 10/2009 | King et al. |
| 2009/0264489 A1 | 10/2009 | Hildebrand et al. |
| 2009/0264490 A1 | 10/2009 | Zanella et al. |
| 2009/0264491 A1 | 10/2009 | McKay et al. |

* cited by examiner

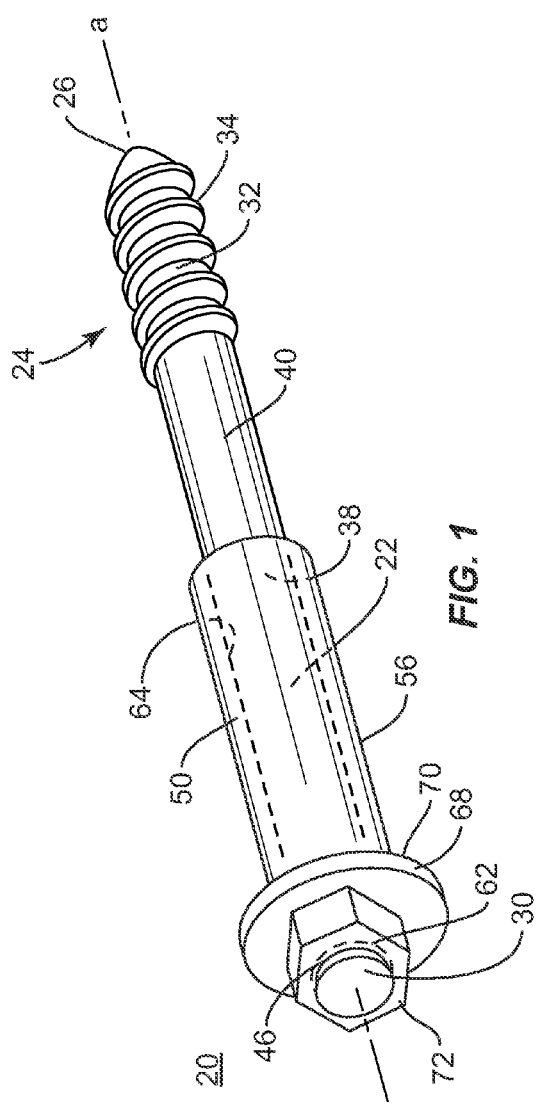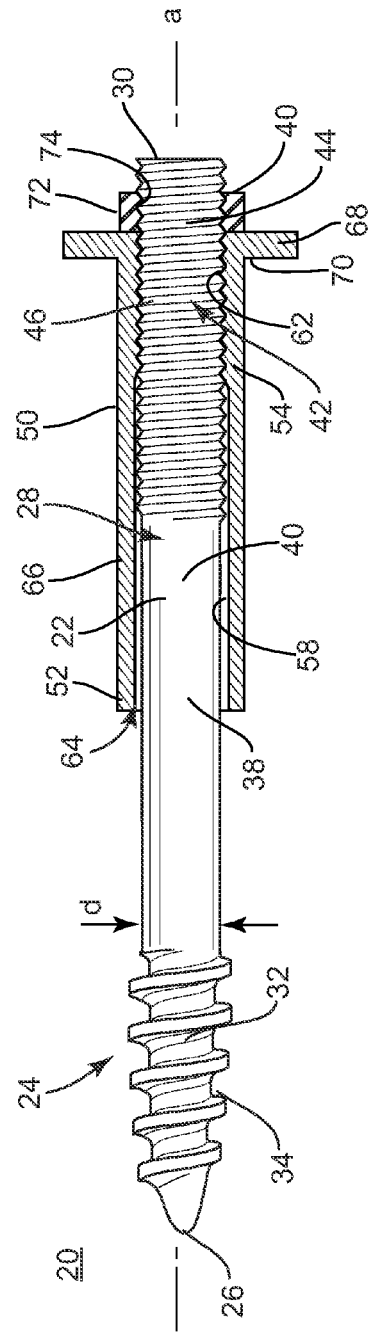

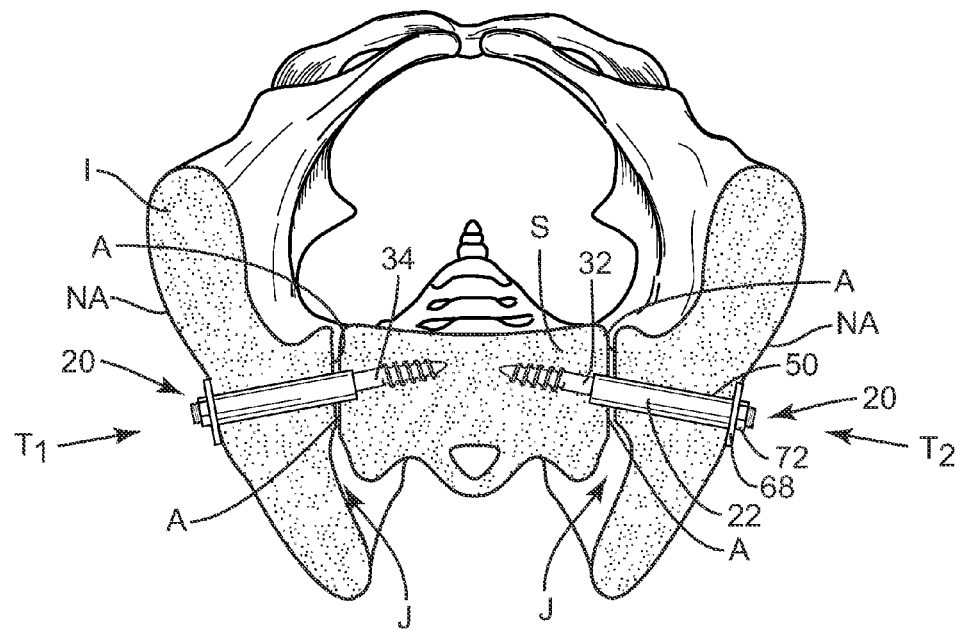
FIG. 5
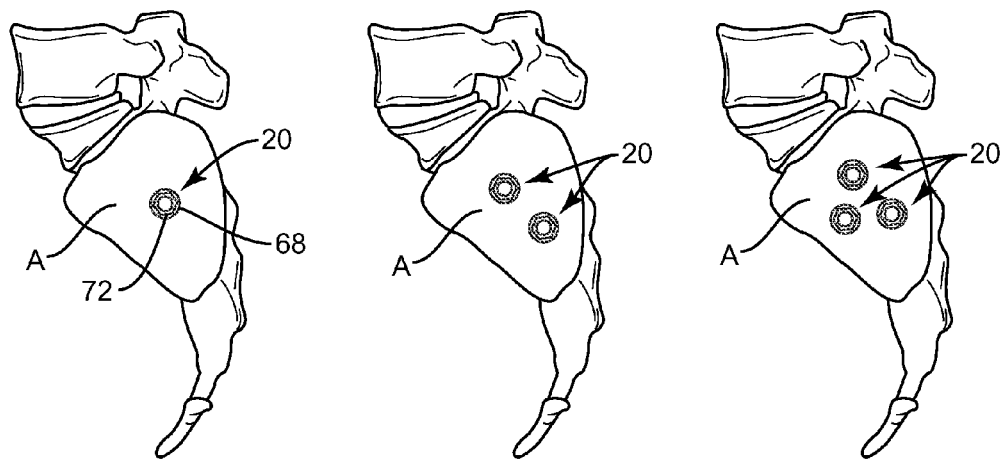
FIG. 6   FIG. 7   FIG. 8

IMPLANT SYSTEM AND METHOD FOR STABILIZATION OF A SACRO-ILIAC JOINT

TECHNICAL FIELD

The present disclosure generally relates to medical devices for the treatment of musculoskeletal disorders, and more particularly to an implant system and method for treating the sacro-iliac joint.

BACKGROUND

The sacroiliac (SI) joint is a diarthrodial joint that joins the sacrum to the ilium bones of the pelvis. In the SI joint, the sacral surface has hyaline cartilage that moves against fibrocartilage of the iliac surface. The spinal column is configured so that the weight of an upper body rests on the SI joints at the juncture of the sacrum and ilia. Stress placed on the SI joints in an upright position of the body makes the lower back susceptible to injury.

Disorders of the SI joint can cause low back and radiating buttock and leg pain in patients suffering from degeneration and laxity of the SI joint. In some cases, the SI joint can undergo dehydration and destabilization, similar to other cartilaginous joints, which causes significant pain. The SI joint is also susceptible to trauma and degeneration, from fracture and instability. It is estimated that disorders of the SI joint are a source of pain for millions of people suffering from back and radicular symptoms.

Non-surgical treatments, such as medication, injection, mobilization, rehabilitation and exercise can be effective, however, may fail to relieve the symptoms associated with these disorders. Surgical treatment of these disorders includes stabilization and/or arthrodesis procedures, which may employ fixation devices. Arthrodesis may include immobilization of a joint. The present disclosure describes an improvement over these prior art technologies.

SUMMARY OF THE INVENTION

Accordingly, an implant system and method is provided for treating the SI joint. It is contemplated that the system may include an implant configured for disposal with the SI joint. It is further contemplated that the implant system and method may be employed for an arthrodesis treatment.

In one particular embodiment, in accordance with the principles of the present disclosure, a sacro-iliac implant is provided. The sacro-iliac implant is adapted to immobilize opposing naturally separated surfaces of a sacro-iliac joint. The sacro-iliac implant includes a body defining a longitudinal axis and extending from a first portion having an outer surface configured for fixation with a sacrum of the sacro-iliac joint to a second portion having an outer surface being spaced apart and non-continuous with the outer surface of the first portion. A sleeve is disposed about the body and configured for implantation within at least an ilium of the sacro-iliac joint. The sleeve extends from a first portion having a substantially even inner surface configured for axial slidable movement relative to the body to a second portion having an inner surface and a flange disposed to engage an outer non-articular surface of the ilium. The inner surface of the second portion of the sleeve is engageable with the outer surface of the second portion of the body to cause axial translation of the body relative to the sleeve in a configuration such that naturally separated articular surfaces of the sacrum and ilium are drawn into fixation to immobilize the sacro-iliac joint.

In one embodiment, a sacro-iliac implant system is provided that includes at least one implant. The implant defines a longitudinal axis and extends from a first portion having an outer surface configured for fixation with a sacrum of the sacro-iliac joint to a second portion having an outer surface being spaced apart and non-continuous with the outer surface of the first portion of the body. A sleeve is disposed about the body and configured for implantation within at least an ilium of the sacro-iliac joint. The sleeve extends from a first portion having a substantially even inner surface configured for axial slidable movement relative to the body to a second portion having an inner surface and a flange disposed to engage an outer non-articular surface of the ilium. The inner surface of the second portion of the sleeve is engageable with the outer surface of the second portion of the body to cause axial translation of the body relative to the sleeve in a configuration such that naturally separated articular surfaces of the sacrum and ilium are drawn into fixation to immobilize the sacro-iliac joint. The body defines an axial cavity extending through the second portion of the body to a plurality of transverse openings disposed adjacent the first portion of the body. At least one biologically compatible agent is disposable within the axial cavity and the transverse openings, and is configured to be eluted or expelled into the sacro-iliac joint.

In one embodiment, a method for treating a sacro-iliac joint is provided. The method includes the steps of: providing at least one implant, similar to those described herein; preparing the sacrum and ilium of the sacro-iliac joint for disposal of the at least one implant therein; delivering the at least one implant to the prepared sacrum and ilium such that at least the outer surface of the first portion of the body is fixed within the sacrum, and the body and the sleeve extend through the ilium such that the flange is disposed for engagement with the outer non-articular surface of the ilium; and translating the body relative to the sleeve such that naturally separated articular surfaces of the sacrum and ilium are drawn into fixation to immobilize the sacro-iliac joint.

BRIEF DESCRIPTION OF THE DRAWINGS

The present disclosure will become more readily apparent from the specific description accompanied by the following drawings, in which:

FIG. 1 is a perspective view of one particular embodiment of an implant system in accordance with the principles of the present disclosure;

FIG. 2 is a side view of the implant system shown in FIG. 1;

FIG. 5 is a plan view, in part cross-section of the implant system and the region shown in FIG. 4;

FIG. 6 is a side view of the implant system, partially shown in phantom, and the region shown in FIG. 5;

FIG. 7 is a side view of one embodiment of the implant system, partially shown in phantom, and the region shown in FIG. 3;

FIG. 8 is a side view of one embodiment of the implant system, partially shown in phantom, and the region shown in FIG. 3;

Like reference numerals indicate similar parts throughout the figures.

DETAILED DESCRIPTION OF THE INVENTION

Figure 3:
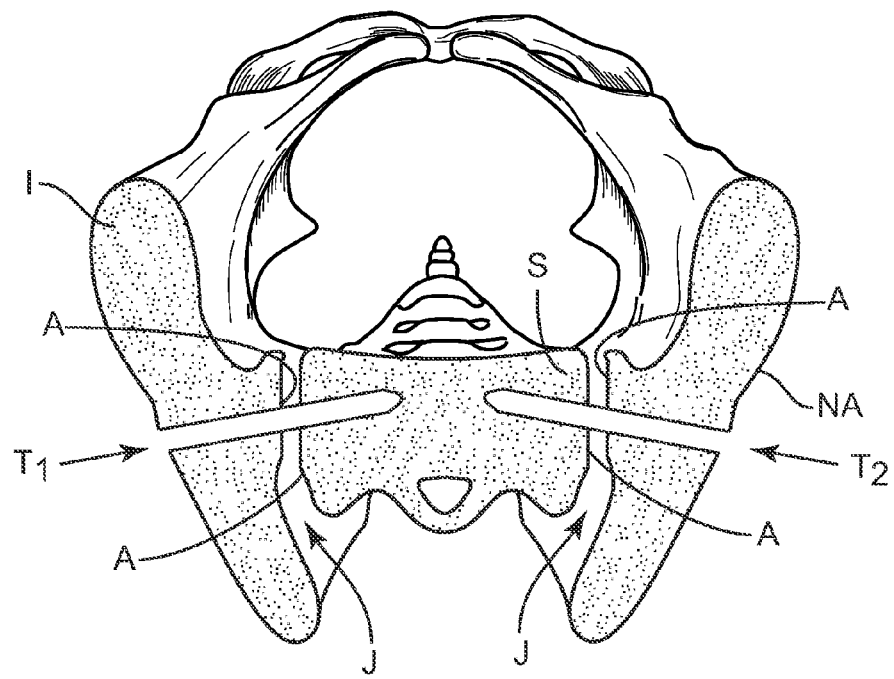
FIG. 3 is a plan view, in part cross section, of a sacro-iliac/ilio-pelvic region.

The exemplary embodiments of the sacro-iliac implant system and methods of use disclosed are discussed in terms of medical devices for the treatment of musculoskeletal disorders and more particularly, in terms of an implant system and method for treating the sacro-iliac joint. It is envisioned that the implant system and methods of use disclosed provide stability by fusing the sacro-iliac joint to reduce or alleviate pain. It is further envisioned that the present disclosure may be employed to treat musculoskeletal disorders including sacro-Iliac dysfunction or syndrome, dehydration, destabilization, laxity, tumor, spinal disorders and other orthopedic disorders. It is contemplated that the present disclosure may be employed with surgical treatments, including open surgery, percutaneous and minimally invasive procedures of such disorders, such as, for example, arthrodesis including fusion, bone graft and implantable prosthetics. It is further contemplated that the present disclosure may be employed with other osteal and bone related applications, including those associated with diagnostics and therapeutics. The disclosed implant system and methods may be employed in a surgical treatment with a patient in a prone or supine position, employing a posterior, lateral, inferior, posterior-inferior, superior or anterior approach. The present disclosure may be employed with procedures for treating the lumbar, cervical, thoracic and pelvic regions of a spinal column.

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of an implant system, related components and exemplary methods of employing the implant system in accordance with the principles of the present disclosure. Alternate embodiments are also disclosed. Reference will now be made in detail to the exemplary embodiments of the present disclosure, which are illustrated in the accompanying figures. Turning now to FIGS. 1-6, there are illustrated components of a sacro-iliac implant system in accordance with the principles of the present disclosure.

The components of the implant system are fabricated from materials suitable for medical applications, including metals, synthetic polymers, ceramics, bone, biocompatible materials and/or their composites, depending on the particular application and/or preference of a medical practitioner. For example, the components of the implant system may be monolithically formed, integrally connected or include fastening elements and/or instruments, as described herein, can be fabricated from materials such as commercially pure titanium, titanium alloys, Grade 5 titanium, super-elastic titanium alloys, cobalt-chrome alloys, stainless steel alloys, superelastic metallic alloys (e.g. Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-$BaSO_4$ composites, ceramics and composites thereof such as calcium phosphate (e.g. SKELITE™ manufactured by Biologix Inc.), rigid polymers including polyphenylene, polyamide, polyimide, polyetherimide, polyethylene, polyurethanes of any durometer, epoxy, silicone, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Different components of the implant system may have alternative material composites to achieve various desired characteristics such as strength, rigidity, elasticity, compliance, biomechanical performance, durability and radiolucency or imaging preference. The components of the implant system may also be fabricated from a heterogeneous material such as a combination of two or more of the above-described materials.

It is envisioned that the components of the implant system can be manufactured via various methods. For example, the body, sleeve and locking element can be manufactured and assembled via injection-molding, insert-molding, overmolding, compression molding, transfer molding, co-extrusion, pultrusion, dip-coating, spray-coating, powder-coating, porous-coating, milling from a solid stock material, and their combinations. One skilled in the art, however, will realize that such materials and fabrication methods suitable for assembly and manufacture, in accordance with the present disclosure, would be appropriate.

The sacro-iliac implant system includes a sacro-iliac implant 20, which is configured, for example, to treat sacro-iliac joint disorders including those caused by degeneration or trauma. Sacro-iliac implant 20 is adapted to immobilize opposing naturally separated surfaces of a sacro-iliac joint. It is contemplated that sacro-iliac implant 20 may be employed for arthrodesis applications, as will be described.

Sacro-iliac implant 20 includes a body 22 that defines a longitudinal axis a. Body 22 extends from a first portion 24, which includes a distal end 26 of body 22, to a second portion 28, which includes a proximal end 30 of body 22. Body 22 has a diameter d, which is generally uniform along its entire length. It is contemplated that diameter d may be uniformly increasing or decreasing, or have alternate diameter dimensions adjacent first portion 24 and/or second portion 28. It is further contemplated that diameter d may be in a range of approximately 2 millimeters (mm) to 20 mm, and preferably in a range of approximately 5 mm to 15 mm.

Body 22 is configured for disposal within a body cavity formed in a sacro-iliac joint J. It is contemplated that the body cavity can be defined by tissues of sacro-iliac joint J, which include bone, cartilage and/or other tissues. Distal end 26 has a sharpened tip configuration for penetrating tissues, including bone. It is contemplated that body 22 may have a solid, hollow, porous or cage configuration. It is further contemplated that the overall and/or cross-sectional geometry of body 22 may have various configurations, for example, round, oval, oblong, triangular, rectangular, polygonal, irregular, uniform, non-uniform, consistent or variable.

First portion 24 includes an anchoring portion, such as, for example, a threaded shaft 32 that defines an outer surface 34 configured for threaded fixation with a sacrum S of sacro-iliac joint J. Shaft 32 has a cylindrical cross section and is transarticular and penetrates tissues, including bone, of sacrum S to secure sacro-iliac implant 20 with sacro-iliac joint J for stabilization and immobilization thereof. It is envisioned that all or only a portion of the anchoring portion may be disposed with sacrum S, and that a portion of the anchoring portion may be disposed with an ilium I of sacro-iliac joint J.

It is contemplated that threaded shaft 32 may have alternate cross section configurations, such as, for example, those described herein. It is envisioned that all or only a portion of the anchoring portion may have alternate surface configurations, for alternative fixation configurations with a body cavity, such as, for example, threaded, non-threaded, arcuate, undulating, substantially smooth, rough, spiked, semi-porous, dimpled and/or polished, textured for friction fit and/or oversized for pressure fit to facilitate fixation with tissues, including bone, of sacrum S. It is further envisioned that first portion 24 may include fastening elements such as anchors, barbs, spikes, detents and/or openings.

Second portion 28 includes a first diameter portion 38 having a substantially even outer surface 40 and a compression portion, such as, for example, a second diameter portion 42. Second diameter portion 42 includes a threaded shaft 44 that defines an outer surface 46. Outer surface 40 is disposed between outer surface 34 and outer surface 46 such that outer surface 46 is spaced apart and non-continuous with outer surface 34.

A sleeve 50 is disposed about body 22 and configured for implantation within at least ilium I of sacro-iliac joint J. Sleeve 50 extends from a first portion 52 to a second portion 54 and defines an outer surface 56. Sleeve 50 is configured for disposal within a body cavity formed in sacro-iliac joint J. It is contemplated that sleeve 50 may be disposed in ilium I and/or sacrum S. It is further contemplated that sleeve 50 may have a porous or cage configuration. It is envisioned that the overall and/or cross-sectional geometry of body 22 may have various configurations, for example, those alternatives described herein.

First portion 52 defines a substantially even inner surface 58 configured for slidable engagement with outer surface 40. Inner surface 58 supports first diameter portion 38 such that body 22 is axially slidable relative to sleeve 50. Second portion 54 includes a compression portion, such as, for example, a threaded inner surface 62 configured for mating engagement with threaded outer surface 46 to facilitate axial translation of body 22 relative to sleeve 50, as will be described. Surfaces 58, 62 define an inner cavity 64 of sleeve 50. Surfaces 58, 62 and outer surface 56 define a circumferential wall 66. It is envisioned that the cross section of inner cavity 64 may have various configurations such as, for example, those alternatives described herein.

Second portion 54 includes a flange 68 disposed to engage an outer non-articular surface NA of ilium I. Flange 68 includes a portion of threaded inner surface 62. It is envisioned that all or only a portion of the surface of flange 68 may have alternate surface configurations for fixation with outer non-articular surface NA, such as, for example, those alternatives described herein. In operation of sacro-iliac implant 20, outer surface 34 is fixed with the tissues of sacrum S, as described. Sleeve 50 is mounted with body 22 such that outer surface 40 is slidably supported by inner surface 58. The threads of outer surface 46 are rotatably received by the threads of inner surface 62, which extend from second portion 54 through flange 68, in a male/female engagement.

As sleeve 50 is relatively rotated about body 22, the threads of surfaces 46, 62 cooperatively engage such that sleeve 50 moves relative to body 22 along longitudinal axis a to facilitate axial translation of sleeve 50. With first portion 24 anchored in sacrum S, such axial translation of sleeve 50 causes a surface 70 of flange 68 to be drawn into engagement with outer non-articular surface NA of ilium I. With first portion 24 anchored in sacrum S and surface 70 disposed in engagement with outer non-articular surface NA, further rotation of sleeve 50 relative to body 22, axially translates sleeve 50 relative to body 22 in a configuration to draw naturally separated articular surfaces A of sacrum S and ilium I into fixation to immobilize sacro-iliac joint J.

Implant 20 includes a locking element, such as, for example, a lock nut 72, which defines a threaded inner surface 74. Upon fixation of articular surfaces A of sacrum S and ilium I, lock nut 72 is rotated onto threaded shaft 44 and into securement with flange 68 to lock implant into a fixation configuration, according to the requirements of a particular surgical application. Lock nut 72 is configured to prevent axial translation of body 22 relative to sleeve 50. Upon fixation of implant 20 with sacro-iliac joint J, any excess portion of body 22 may be removed from implant 20, such as by severing, cutting and/or fracture. It is contemplated that the locking element may include a ratchet type locking configuration. In one embodiment, the locking element may include an axial ratchet configuration such that body 22 and sleeve 50 have a reciprocal tooth, such as, for example, a pawl, and notch, such as, for example, a gear, arrangement whereby as body 22 linearly translates in only one direction, such as the trajectories discussed below, while preventing motion in the opposite direction.

It is envisioned that body 22, sleeve 50 and/or lock nut 72 can be variously configured and dimensioned with regard to size, shape, thickness, geometry and material. Each of body 22, sleeve 50 and/or lock nut 72 may also be formed of one or a plurality of elements such as spaced apart portions, staggered patterns and mesh. It is envisioned that the particular geometry and material parameters of body 22, sleeve 50 and/or lock nut 72 may be selected to modulate the flexibility or stiffness of sacro-iliac implant 20, such as those examples discussed herein. For example, each of body 22, sleeve 50 and/or lock nut 72 can be configured to have varying ranges or degrees of flexibility or stiffness such as rigid, compliant, or reinforced. Depending on the flexibility or stiffness of body 22, sleeve 50 and/or lock nut 72, the flexibility or stiffness of sacro-iliac implant 20 can be contoured according to the requirements of a particular application. It is contemplated that the ability to vary stiffness of sacro-iliac implant 20 promotes fusion of the elements of sacro-iliac joint J. It is envisioned that the components of sacro-iliac implant 20 may be monolithically formed, integrally connected or arranged with attaching elements.

It is contemplated that the implant system can include a plurality of sacro-iliac implants 20, similar to that described above with regard to FIGS. 1-6. For example, as shown in FIG. 7, the implant system includes a pair of sacro-iliac implants 20. In another example, as shown in FIG. 8, the implant system includes three sacro-iliac implants 20. It is contemplated that employing the plurality of sacro-iliac implants 20 can optimize the stability of sacro-iliac joint J. The plurality of sacro-iliac implants 20 can be inserted through the same or an alternate trajectory. The plurality of sacro-iliac implants 20 can be oriented in a side by side engagement, spaced apart and/or staggered. It is envisioned that one or all of the plurality of sacro-iliac implants 20 may be inserted via a trajectory oriented from an anterior, posterior, superior or inferior direction, similar to that described herein. It is further envisioned that one or a plurality of sacro-iliac implants 20 may be used.

In assembly, operation and use, the implant system including sacro-iliac implant 20 is employed with a surgical procedure for treatment of a sacro-iliac joint J of a patient, as discussed herein. The implant system may also be employed with other surgical procedures. In particular, the implant system is employed with a surgical arthrodesis procedure, such as, for example, fusion for treatment of an applicable condition or injury of an affected sacro-iliac joint J, as shown in FIGS. 3-6. It is contemplated that the implant system including sacro-iliac implant 20 may be employed during a surgical fusion procedure for treatment of a condition or injury, such as, degeneration or fracture.

In use, to treat the affected section of sacro-iliac joint J, a medical practitioner obtains access to a surgical site including sacro-iliac joint J in any appropriate manner, such as through incision and retraction of tissues. It is envisioned that the implant system may be used in any existing surgical method or technique including open surgery, mini-open surgery, minimally invasive surgery and percutaneous surgical implantation, whereby sacro-iliac joint J is accessed through a mini-incision, or sleeve that provides a protected passageway to the area. Once access to the surgical site is obtained, the particular surgical procedure is performed for treating the sacro-iliac joint disorder. The implant system is then employed to augment the surgical treatment. The implant system can be delivered or implanted as a pre-assembled device or can be assembled in situ. The implant system may be completely or partially revised, removed or replaced in situ. It is contemplated that one or all of the components of the implant system can be delivered to the surgical site via manual manipulation and/or a free hand technique.

Trajectories $T_1$, $T_2$, as shown in FIG. 3, are defined for insertion of the components of sacro-iliac implant 20 within sacro-iliac joint J. The components of sacro-iliac implant 20 are inserted via the protected passageway along each of the defined trajectories $T_1$, $T_2$ into sacro-iliac joint J. Separate body cavities of sacro-iliac joint J are prepared along each of trajectories $T_1$, $T_2$ for disposal of sacro-iliac implant 20. It is contemplated that a guide wire and/or a trocar-cannula assembly may be employed as an instrument for gaining access to the surgical site and/or defining the trajectories.

The protected passageway includes a dilator/delivery tube (not shown) configured to deliver sacro-iliac implant 20 adjacent to the joint space of sacro-iliac joint J. It is envisioned that the dilator/delivery tube may be configured as an in-situ guidable instrument, and may include an endoscope camera tip for viewing insertion trajectory. It is further envisioned that the components of sacro-iliac implant 20 may include a cavity configured to receive the instrument to facilitate delivery of sacro-iliac implant 20 to sacro-iliac joint J. It is contemplated that the components of sacro-iliac implant 20 and/or other components of the implant system, and the several embodiments of the implant system described herein, may include a connecting portion, opening and/or mechanism, such as, for example, threaded holes, snap-on connects, and quick-connect mechanisms for connection to a delivery instrument for implant disposal, detachable connection and release and removal from the surgical site.

Figure 4:
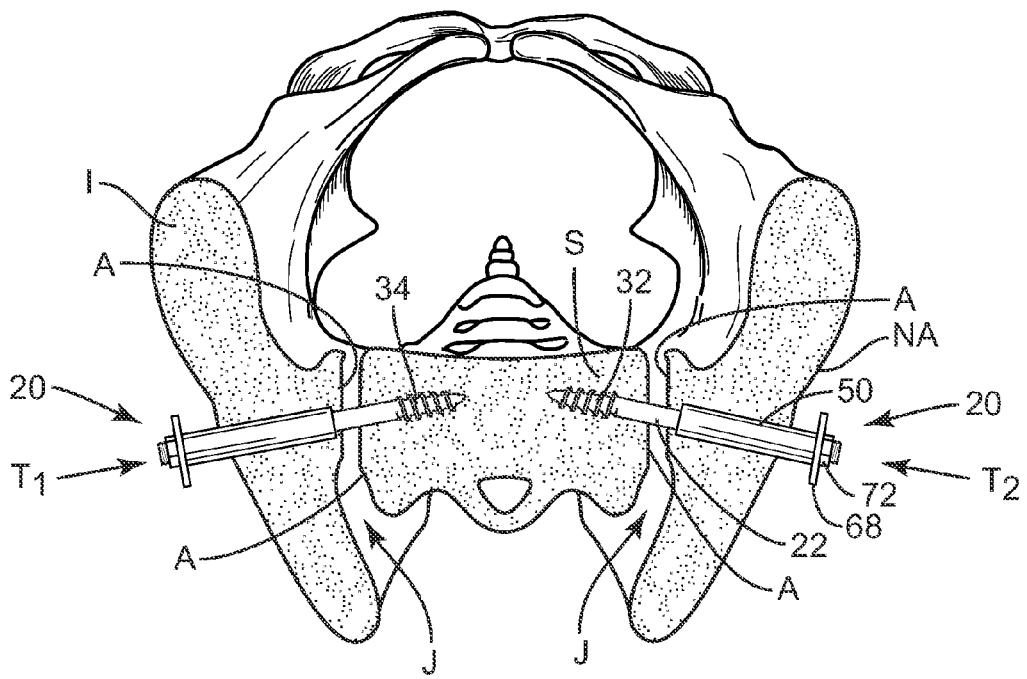
FIG. 4 is a plan view, in part cross section, of the implant system shown in FIG. 1 and the region shown in FIG. 3.

The body cavities are tapped and/or drilled in the joint surfaces of sacro-iliac joint J in an orientation and alignment with sacrum S and ilium I. It is contemplated that a guide instrument (not shown) may be used to facilitate formation of such cavities by providing an alignment device for a surgical drill and/or tap. A first sacro-iliac implant 20 including body 22, with or without sleeve 50, is delivered via the guide instrument to sacro-iliac joint J into alignment with the body cavity along trajectory $T_1$, as shown in FIG. 4. A second sacro-iliac implant 20 is similarly delivered via the guide instrument to sacro-iliac joint J into alignment with the body cavity along trajectory $T_2$. For each sacro-iliac implant 20, threaded shaft 32 is threaded with the joint surfaces of sacro-iliac joint J such that outer surface 34 is fixed with the tissues of sacrum S, as described above.

Sleeve 50 is mounted with body 22 such that outer surface 40 is slidably supported by inner surface 58. The threads of outer surface 46 are rotatably received by the threads of inner surface 62 in a male/female engagement. Sleeve 50 is manipulated by a practitioner and/or an appropriate instrument to relatively rotate about body 22 such that sleeve 50 moves relative to body 22 along longitudinal axis a to facilitate axial translation of sleeve 50, as described above.

With first portion 24 anchored in sacrum S via outer surface 34, axial translation of sleeve 50 causes flange 68 to be drawn into engagement with outer non-articular surface NA of ilium I. With first portion 24 anchored in sacrum S and surface 70 disposed in engagement with outer non-articular surface NA, further rotation of sleeve 50 relative to body 22, axially translates sleeve 50 relative to body 22 in a configuration to draw naturally separated articular surfaces A of sacrum S and ilium I into fixation to secure, stabilize and immobilize sacro-iliac joint J, as shown in FIGS. 5-6.

Lock nut 72 is rotated onto threaded shaft 44 and into securement with flange 68 to lock sacro-iliac implant 20 into a fixation configuration for fusing sacro-iliac joint J. Upon fixation of sacro-iliac implant 20 with sacro-iliac joint J, any excess portion of body 22 may be removed from sacro-iliac implant 20. This configuration of sacro-iliac implant 20 tensions the joint ligaments of sacro-iliac joint J. It is envisioned that trajectory $T_1$ may be oriented perpendicular, parallel, angularly offset, offset, cruciate and/or staggered relative to trajectory $T_2$.

In one embodiment, the sacro-iliac implant system includes fastening elements, such as, for example, screws (not shown) configured for fixation with articular surfaces A external to sacro-iliac implant 20. The screws are employed to secure joint surfaces and provide complementary stabilization and immobilization to sacro-iliac joint J. It is envisioned that sacro-iliac implant 20 may include locking structure such as, for example, clips, hooks, adhesives and/or flanges. It is further envisioned that in joint fusion applications, the components of sacro-iliac implant 20 includes voids, cavities and/or openings for including therapeutic polynucleotides or polypeptides and bone growth promoting material, such as those described herein, which can be packed or otherwise disposed therein.

For example, the components of sacro-iliac implant 20 may include at least one agent including biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, biologically active agents coated onto the exterior of the components of sacro-iliac implant 20 and/or applied thereto for gradual release such as by blending in a bioresorbable polymer that releases the biologically active agent or agents in an appropriate time dependent fashion as the polymer degrades within the patient. Suitable biologically active agents include, for example, bone morphogenic protein (BMP), cytokines, osteoconductive and/or osteoinductive material such as HA and/or osteoinductive agent, either partially or completely to enhance osteointegration and fusion across sacro-iliac joint J, and/or for enhanced bony fixation to the treated area. It is contemplated that such materials may include a combination of materials such as, for example, an HA coating with BMP for improved fusion rate. It is further contemplated that such materials may include pharmacological agents as described herein. It is envisioned that the components of the sacro-iliac implant system may include large cavities or slots configured to receive fasteners and/or pack bone graft, such as, for example, autograft, allograft, bone chips, demineralized bone matrix, calcium phosphate, HA, and bone growth agents in a carrier matrix for enhancing fusion.

The components of sacro-iliac implant 20 can be made of radiolucent materials such as polymers. Radiomarkers may be included for identification under x-ray, fluoroscopy, CT or other imaging techniques.

In one embodiment, the sacro-iliac implant system includes sacro-iliac implant 20, similar to that described above, which is employed with a sacro-iliac implant joint spacer (not shown) in a surgical procedure for treatment of sacro-iliac joint J of a patient. The sacro-iliac implant joint spacer is inserted with sacro-iliac joint J to space apart articular joint surfaces A. The sacro-iliac implant joint spacer is delivered the joint space of sacro-iliac joint J and manipulated to engage opposing articular surfaces A. The body of the sacro-iliac implant joint spacer is configured for compliant engagement with articular surfaces A to space apart opposing articular surfaces A. The sacro-iliac implant joint spacer defines a transverse opening that supports at least a portion of body 22 and/or sleeve 50. It is contemplated that articular surfaces A may be prepared via debriding and/or decorticating such that the sacro-iliac implant joint spacer may be implanted with the prepared articular surface(s).

Figure 9:
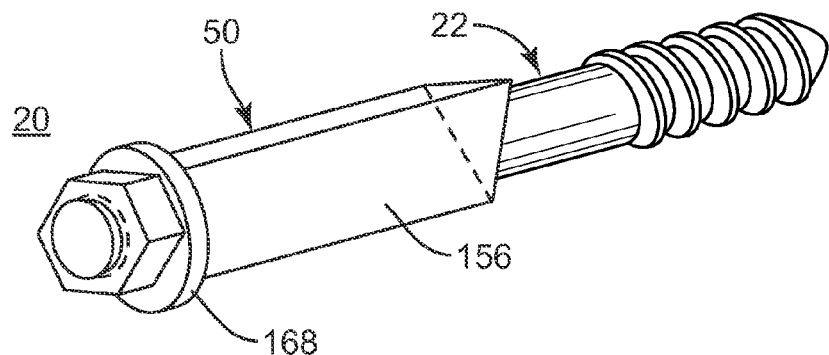
FIG. 9 is a perspective view of one embodiment of the implant system shown in FIG. 1.

In one embodiment, as shown in FIG. 9, sacro-iliac implant 20, similar to that described above, includes sleeve 50. Sleeve 50 includes a flange 168, similar to flange 68 described above, having a first cross section configuration, such as, for example, a circular disc configuration and an outer surface 156, similar to outer surface 56 described above, having a different second cross section configuration, such as, for example, a triangular cross section configuration. The triangular cross section configuration of outer surface 156 prevents loosening and/or backout of sacro-iliac implant 20 from the joint surfaces of sacro-iliac joint J, such as, for example, ilium I. It is contemplated that the triangular cross section configuration of outer surface 156, when extended between ilium I and sacrum S, prevents rotation of sacro-iliac joint J. It is envisioned that sleeve 50 includes inner surface 58 (FIG. 2) for support of body 22, described above.

Figure 10:
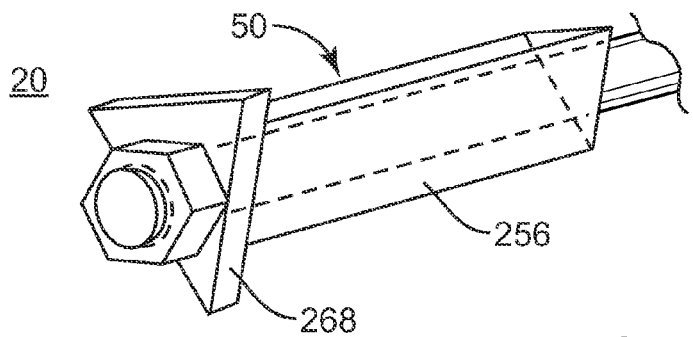
FIG. 10 is a cutaway perspective view of one embodiment of the implant system shown in FIG. 1.
Figure 11:
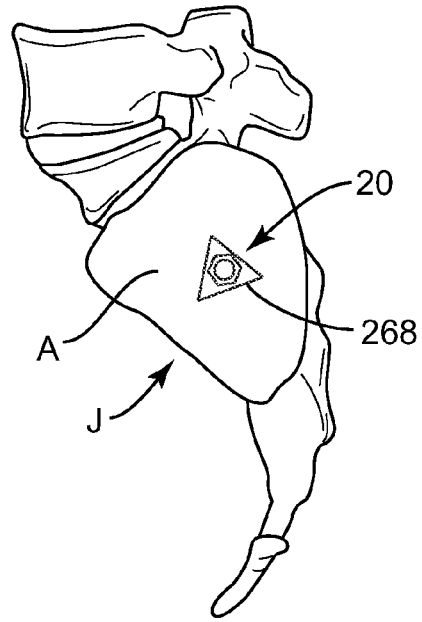
FIG. 11 is a side view of the implant system shown in FIG. 10, partially in phantom, and the region shown in FIG. 3.

In one embodiment, as shown in FIGS. 10-11, sacro-iliac implant 20, similar to that described above, includes sleeve 50. Sleeve 50 includes a flange 268, similar to flange 68 described above, having a first cross section configuration, such as, for example, a triangular configuration and an outer surface 256, similar to outer surface 56 described above, having a second cross section configuration, such as, for example, a triangular cross section configuration. The triangular cross section configuration of flange 268 and/or outer surface 256 prevents loosening and/or backout of sacro-iliac implant 20 from the joint surfaces of sacro-iliac joint J. It is contemplated that the triangular cross section configuration of outer surface 256, when extended between ilium I and sacrum S, prevents rotation of sacro-iliac joint J.

Figure 12:
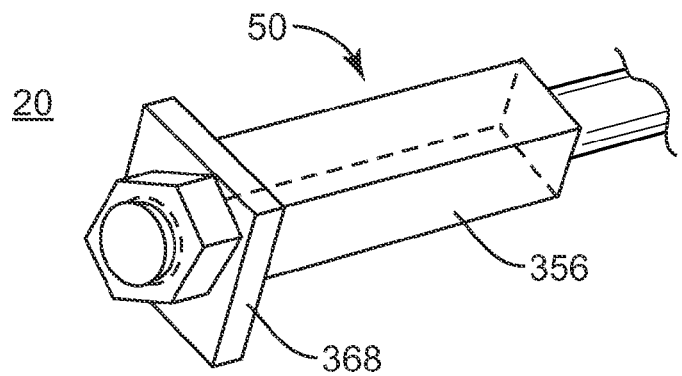
FIG. 12 is a cutaway perspective view of one embodiment of the implant system shown in FIG. 1.
Figure 13:
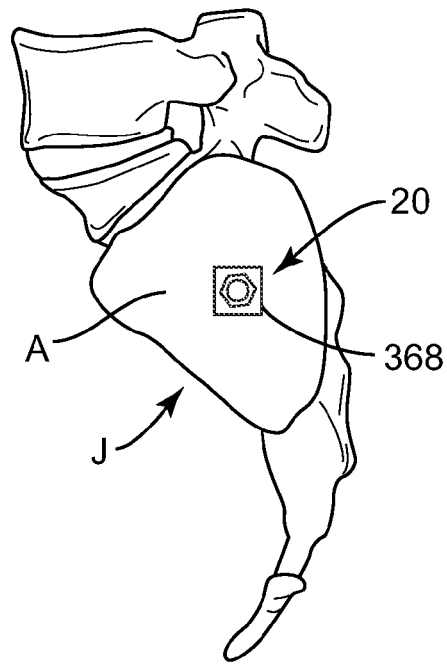
FIG. 13 is a side view of the implant system shown in FIG. 12, partially in phantom, and the region shown in FIG. 3.

In one embodiment, as shown in FIGS. 12-13, sacro-iliac implant 20, similar to that described above, includes sleeve 50. Sleeve 50 includes a flange 368, similar to flange 68 described above, having a first cross section configuration, such as, for example, a square/rectangular configuration and an outer surface 356, similar to outer surface 56 described above, having a second cross section configuration, such as, for example, a square/rectangular cross section configuration. The square/rectangular cross section configuration of flange 368 and/or outer surface 356 prevents loosening and/or backout of sacro-iliac implant 20 from the joint surfaces of sacro-iliac joint J. It is contemplated that the square/rectangular cross section configuration of flange 368 and/or outer surface 356, when extended between ilium I and sacrum S, prevents rotation of sacro-iliac joint J.

Figure 14:
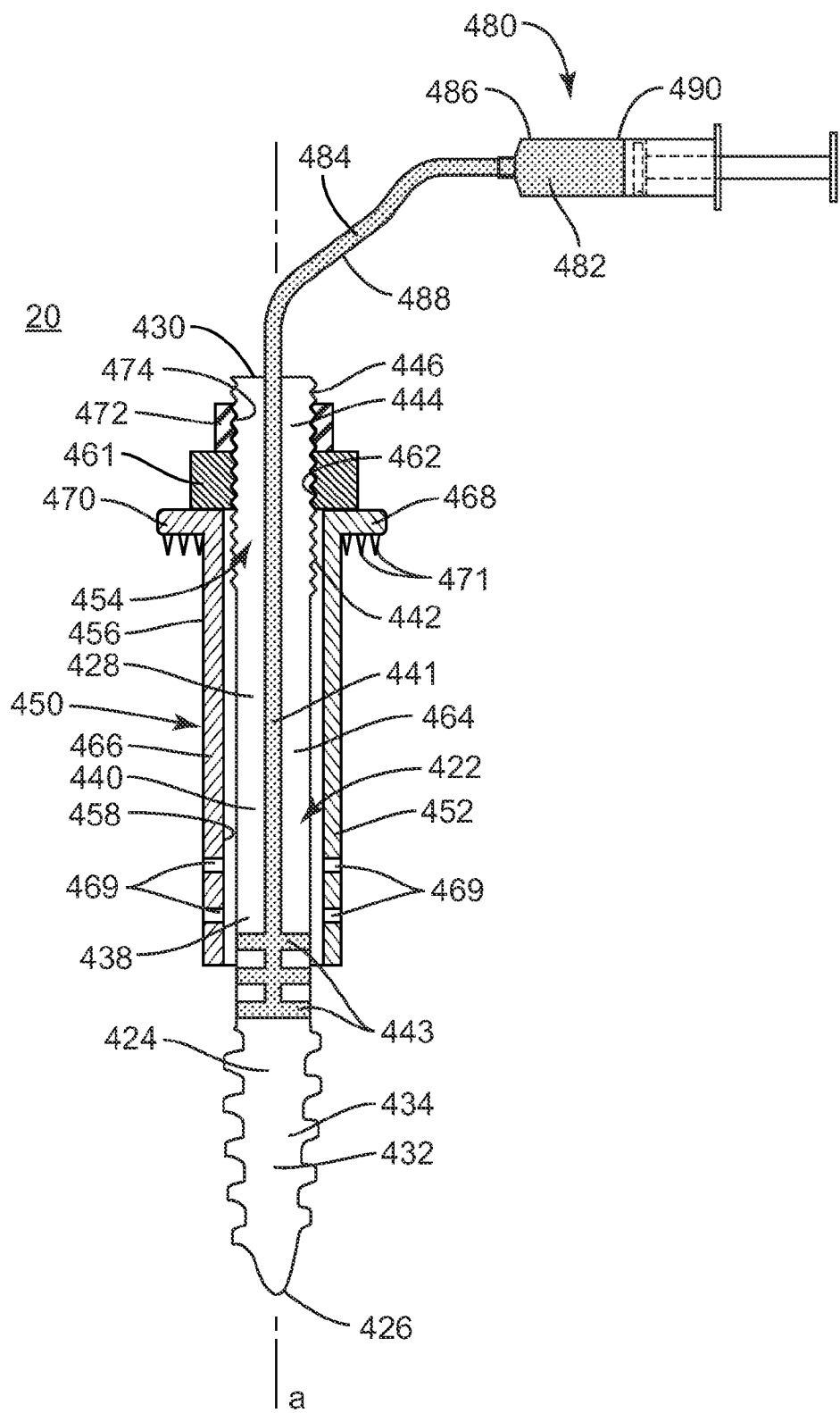
FIG. 14 is a plan view, in part cross section, of one embodiment of an implant system in accordance with the principles of the present disclosure.

In one embodiment, as shown in FIG. 14, sacro-iliac implant 20, similar to the apparatus and method of use described above with regard to FIGS. 1-6, includes a body 422 that defines a longitudinal axis a. Body 422 extends from a first portion 424, which includes a distal end 426 of body 422, to a second portion 428, which includes a proximal end 430 of body 422.

Body 422 is configured for disposal within a body cavity formed in sacro-iliac joint J (FIGS. 3-6). Distal end 426 has a sharpened tip configuration for penetrating tissues, including bone. First portion 424 includes a threaded shaft 432 that defines an outer surface 434 configured for threaded fixation with sacrum S.

Second portion 428 includes a first diameter portion 438 having a substantially even outer surface 440 and a second diameter portion 442. Second diameter portion 442 includes a threaded shaft 444 that defines an outer surface 446. Outer surface 440 is disposed between outer surface 434 and outer surface 446 such that outer surface 446 is spaced apart and non-continuous with outer surface 434.

Second portion 428 of body 422 defines an axial cavity 441 extending therethrough to a plurality of transverse openings 443 disposed adjacent first portion 424. Axial cavity 441 and transverse openings 443 are configured for disposal of at least one biologically compatible agent, which is expelled or eluted into sacro-iliac joint J., as will be described. Transverse openings 443 are disposed sequentially in parallel along body 422. It is envisioned that one, a plurality or all of transverse openings 443 may be oriented perpendicular, parallel, angularly offset, offset, cruciate and/or staggered relative to axial cavity 441. It is further envisioned that one, a plurality or all of transverse openings 443 may be oriented perpendicular, parallel, angularly offset, offset, cruciate and/or staggered relative to other openings 443.

A sleeve 450 is disposed about body 422 and configured for implantation within at least ilium I of sacro-iliac joint J. Sleeve 450 extends from a first portion 452 to a second portion 454 and defines an outer surface 456. Sleeve 450 is configured for disposal within a body cavity formed in sacro-iliac joint J.

First portion 452 defines a substantially even inner surface 458, which extends through a portion of second portion 454. Inner surface 458 is configured for slidable engagement with outer surface 440. Inner surface 458 supports first diameter portion 438 such that body 422 is axially slidable relative to sleeve 450. Second portion 454 includes a compression portion, such as, for example, a compression element 461 that defines a threaded inner surface 462 configured for mating engagement with threaded outer surface 446 to facilitate axial translation of body 422 relative to sleeve 450, as will be described. Surface 458 defines an inner cavity 464 of sleeve 450. Surface 458 and outer surface 456 define a circumferential wall 466. It is contemplated that compression element 461 may be employed with other configurations of a body and a sleeve, such as that shown and described with regard to FIGS. 1 and 2.

Second portion 454 includes a flange 468 disposed to engage outer non-articular surface NA. Flange 468 is attached to compression element 461. Flange 468 includes a surface 470 configured to engage outer non-articular surface NA. Surface 470 includes gripping elements, such as, for example, spikes 471 configured to engage and fix flange 468 with outer non-articular surface NA. It is envisioned that surface 470 may have alternate gripping configurations, such as, for example, anchors, barbs, detents, openings, arcuate, undulating, rough, serrations, semi-porous, dimpled and/or textured to facilitate fixation with tissues, including bone. It is further envisioned that surface 470 may include one or a plurality of gripping elements.

Sleeve 450 defines to a plurality of transverse openings 469 in communication with transverse openings 443 to facilitate the at least one biologically compatible agent being expelled or eluted into sacro-iliac joint J. Transverse openings 469 are disposed sequentially in parallel along sleeve 450. It is envisioned that one, a plurality or all of transverse openings 469 may be oriented perpendicular, parallel, angularly offset, offset, cruciate and/or staggered relative to axial cavity 441. It is further envisioned that one, a plurality or all of transverse openings 469 may be oriented perpendicular, parallel, angularly offset, offset, cruciate and/or staggered relative to other openings 469.

In operation of sacro-iliac implant 20, outer surface 434 is fixed with the tissues of sacrum S. Sleeve 450 is mounted with body 422 such that outer surface 440 is slidably supported by inner surface 458. The threads of outer surface 446 are rotatably received by the threads of inner surface 462, which extend through compression element 461, in a male/female engagement.

As compression element 461 is relatively rotated about body 422, the threads of surfaces 446, 462 cooperatively engage such that sleeve 450 moves relative to body 422 along longitudinal axis a to facilitate axial translation of sleeve 450. With first portion 424 anchored in sacrum S, such axial translation of sleeve 450 causes surface 470 to be drawn into engagement with outer non-articular surface NA. With first portion 424 anchored in sacrum S and surface 470 disposed in engagement with outer non-articular surface NA, further rotation of compression element 461 relative to body 422 axially translates sleeve 450 relative to body 422 in a configuration to draw naturally separated articular surfaces A of sacrum S and ilium I into fixation to immobilize sacro-iliac joint J.

Sacro-iliac implant 20 includes a lock nut 472, which defines a threaded inner surface 474. Upon fixation of articular surfaces A of sacrum S and ilium I, lock nut 472 is rotated onto threaded shaft 444 and into securement with flange 468 to lock sacro-iliac implant 20 into a fixation configuration. Lock nut 472 is configured to prevent axial translation of body 422 relative to sleeve 450.

The sacro-iliac implant system includes a delivery instrument 480 configured to deliver at least one biologically compatible agent 482 to axial cavity 441, transverse openings 443 and/or transverse openings 469 to be expelled or eluted into sacro-iliac joint J. Instrument 480 includes a distal portion 484 and a proximal portion 486. Distal portion 484 includes a catheter 488 detachably connected with body 422. Proximal portion 486 includes an injector 490 that fluidly communicates with catheter 488 for delivery of agent 482 to body 422. Injector 490 is actuated to provide the pressure required to expel a flowable agent 482 from injector 490 through catheter 488 and into axial cavity 441.

It is contemplated that instrument 480 may employ various injectors for delivery of a flowable material, such as, for example, a syringe, caulk gun, mechanical injector and/or power injector. It is further contemplated that instrument 480 may employ alternative pressure generating devices such as a pump.

Transverse openings 443 and/or transverse openings 469 are configured to expel and/or elute agent 482 therefrom. Transverse openings 443, transverse openings 469 and/or axial cavity 441 may include one or a plurality of agent reservoirs. The agent reservoirs can be configured as drug depots with medication for pain and may include antibiotics and/or therapeutics. Diffusion of such agents can occur through openings 443 and/or openings 469. It is envisioned that body 422 includes a network of agent diffusing openings 443 and/or openings 469 interconnected and/or in fluid communication. It is contemplated that body 422 and/or each of openings 443 and/or openings 469 may include one or a plurality of agents. Openings 443 and/or openings 469 may be oriented parallel to articular surfaces of a sacro-iliac joint, perpendicular, randomly oriented, and/or configured for multiple directional expulsion or eluting.

It is envisioned that the agent reservoirs contain active agents and may include one or a plurality of therapeutic agents and/or pharmacological agents for release, including sustained release, into sacro-iliac joint J to treat, for example, pain, inflammation and degeneration. The agents may include pharmacological agents, such as, for example, antibiotics, pain medications, analgesics, anesthetics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, clonidine, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics.

The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen) and Rapamuen™ (sirolimus).

It is envisioned that openings 443 and/or openings 469 are capable of accepting at least one agent before, during and/or after implantation with sacro-iliac joint J, holding the at least one agent in a reservoir, and/or delivery in vivo of the at least one agent to tissues of sacro-iliac joint J and tissues surrounding sacro-iliac joint J, including bone. Openings 443 and/or openings 469 may be replenished, via one or a plurality of iterations, with therapeutic and/or pharmacological agents. Agent 482 may be eluted from openings 443 and/or openings 469 via an unstressed, free-flowing fluid communication with joint tissues, including bone. Agent 482 may permeate or diffuse through the material of body 422.

Agent 482 may include bone growth promoting material, such as, for example, bone graft configured for disposal within, about and/or adjacent sacro-iliac joint J. It is envisioned that the bone graft is a particulate material, which may include an osteoconductive material such as hydroxyapatite, an osteoinductive agent such as BMP, Growth and Differentiation Factors proteins (GDF) and/or cytokines. It is contemplated that the bone graft may include therapeutic polynucleotides or polypeptides. It is further contemplated that the bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite, calcium phosphate and calcium sulfite, biologically active agents, for example, gradual release compositions such as by blending in a bioresorbable polymer that releases the biologically active agent or agents in an appropriate time dependent fashion as the polymer degrades within the patient.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A sacro-iliac implant adapted to immobilize opposing naturally separated surfaces of a sacro-iliac (SI) joint, the implant comprising:
    a body defining a longitudinal axis and extending from a first portion having an outer surface configured for fixation with a sacrum of the SI joint to a second portion having an outer surface being spaced apart and non-continuous with the outer surface of the first portion, the body defining an axial cavity disposed in communication with spaced apart transverse openings each extending through the body; and
    a sleeve disposed about the body and configured for implantation within at least an ilium of the SI joint, the sleeve extending from a first portion having a substantially even inner surface configured for axial slidable movement relative to the body to a second portion having an inner surface and a flange disposed to engage an outer non-articular surface of the ilium, the sleeve defines transverse openings,
    the inner surface of the second portion of the sleeve being engageable with the outer surface of the second portion of the body to cause axial translation of the body relative to the sleeve in a configuration such that naturally separated articular surfaces of the sacrum and ilium are drawn into fixation to immobilize the SI joint,
    wherein the body is axially translatable relative to the sleeve between a first configuration in which the transverse openings of the body are spaced apart from the transverse openings of the sleeve and a second configuration in which at least one of the transverse openings of the body is aligned with at least one of the transverse openings of the sleeve.

2. The sacro-iliac implant of claim 1, wherein an outer surface of the sleeve defines a triangular cross-section configuration.

3. The sacro-iliac implant of claim 1, wherein the flange defines a first cross-section configuration and an outer surface of the sleeve defines a second, different cross-section configuration.

4. The sacro-iliac implant of claim 1, wherein the flange defines a circular cross-section configuration and an outer surface of the sleeve defines a triangular cross-section configuration.

5. The sacro-iliac implant of claim 1, further comprising a locking element disposed adjacent the flange and having an inner surface engageable with the outer surface of the second portion of the body to prevent axial translation of the body relative to the sleeve.

6. The sacro-iliac implant of claim 1, wherein the second portion of the sleeve includes a compression element attached to the flange, the compression element including the inner surface of the second portion of the sleeve.

7. The sacro-iliac implant of claim 1, wherein the second portion of the body has a first diameter portion having a substantially even outer surface and a second diameter portion including the outer surface of the second portion.

8. The sacro-iliac implant of claim 1, wherein the flange includes gripping elements configured for engagement with the outer non-articular surface of the ilium.

9. The sacro-iliac implant of claim 1, wherein the transverse openings each extend perpendicular to the longitudinal axis through a section of the body that is free of threads.

10. The sacro-iliac implant of claim 1, wherein the second portion of the body is disposed between a threaded shaft and the first portion of the body, the outer surface of the second portion of body having a cylindrical cross sectional configuration.

11. The sacro-iliac implant of claim 1, wherein the flange comprises a planar lower surface extending perpendicular to the longitudinal axis that is configured to engage the non-articular surface of the ilium.

12. The sacro-iliac implant of claim 1, wherein the flange comprises a lower surface extending perpendicular to the longitudinal axis that is configured to engage the non-articular surface of the ilium, the lower surface comprising a plurality of spikes extending therefrom.

13. The sacro-iliac implant of claim 1, wherein the first portion of the body is non-cannulated.

14. The sacro-iliac implant of claim 1, wherein the transverse openings are disposed sequentially in parallel along the body.

15. The sacro-iliac implant of claim 6, wherein the compression element is rotatable relative to the sleeve.

16. A sacro-iliac implant adapted to immobilize opposing naturally separated surfaces of a sacro-iliac (SI) joint, the implant comprising:

a body defining a longitudinal axis and extending from a first portion having a first thread form configured for fixation with a sacrum of the SI joint to a second portion having a second thread form, an outer surface of the body being free of any projections from the first thread form to the second thread form, the body defining a cavity that is coaxial with the longitudinal axis disposed in communication with a plurality of spaced apart transverse openings each extending perpendicular to the longitudinal axis through the body; and a sleeve disposed about the body and configured for implantation within at least an ilium of the SI joint, the sleeve extending from a first portion having a substantially even inner surface configured for axial slidable movement relative to the body to a second portion having an inner surface and a flange disposed to engage an outer non-articular surface of the ilium, the sleeve comprising transverse openings extending through the sleeve, the inner surface of the second portion of the sleeve a third thread form that engages the second thread form to cause axial translation of the body relative to the sleeve in a configuration such that naturally separated articular surfaces of the sacrum and ilium are drawn into fixation to immobilize the SI joint, wherein the body is axially translatable relative to the sleeve between a first configuration in which each of the transverse openings of the body are positioned within the sleeve and a second configuration in which at least one of the transverse openings of the body is positioned outside of the sleeve.

* * * * *